United States Patent
Chirban et al.

(10) Patent No.: US 12,389,879 B2
(45) Date of Patent: Aug. 19, 2025

(54) INSECT DISPENSING DEVICE

(71) Applicant: CENTRAL GARDEN & PET COMPANY, Walnut Creek, CA (US)

(72) Inventors: Alexander Chirban, Wauwatosa, WI (US); Ernie Katris, Hawthorn Woods, IL (US)

(73) Assignee: CENTRAL GARDEN & PET COMPANY, Walnut Creek, CA (US)

( * ) Notice: Subject to any disclaimer, the term of this patent is extended or adjusted under 35 U.S.C. 154(b) by 121 days.

(21) Appl. No.: 18/481,022

(22) Filed: Oct. 4, 2023

(65) Prior Publication Data

US 2025/0113802 A1    Apr. 10, 2025

(51) Int. Cl.
*A01K 5/01* (2006.01)

(52) U.S. Cl.
CPC .............. *A01K 5/0135* (2013.01); *A01K 5/01* (2013.01)

(58) Field of Classification Search
CPC .................................................. A01K 5/0135
See application file for complete search history.

(56) References Cited

U.S. PATENT DOCUMENTS

| | | | |
|---|---|---|---|
| 3,999,519 A * | 12/1976 | Rodemeyer | A01K 5/02 119/51.01 |
| 4,328,636 A * | 5/1982 | Johnson | A01M 1/106 43/118 |
| 4,825,577 A * | 5/1989 | Brannon | A01K 97/04 D22/136 |
| 5,398,642 A * | 3/1995 | Harwich | A01K 67/30 119/6.5 |
| 5,544,621 A | 8/1996 | Haurilesko | |
| 5,630,374 A * | 5/1997 | Cunningham | A01K 61/85 119/6.5 |
| 6,711,849 B1 * | 3/2004 | Moretti | A01K 97/02 43/44.99 |
| 6,758,162 B1 | 7/2004 | Van Heygen | |
| 7,174,847 B1 * | 2/2007 | Hulteen, III | A01K 63/003 43/132.1 |
| 7,878,146 B2 * | 2/2011 | Vadis | A01K 63/003 119/6.5 |
| 8,186,302 B1 * | 5/2012 | Foster | A23K 40/30 119/51.01 |
| 8,820,268 B2 * | 9/2014 | Valle | A01K 15/025 119/710 |
| 2002/0069829 A1 * | 6/2002 | McMahon | A01K 39/014 119/51.01 |
| 2008/0078328 A1 * | 4/2008 | Orup | A01K 13/003 119/51.01 |
| 2008/0083378 A1 * | 4/2008 | Pearce | A01K 5/0114 119/707 |
| 2012/0325157 A1 * | 12/2012 | Lipscomb | A01K 5/0142 119/52.1 |
| 2022/0142137 A1 * | 5/2022 | Chase | A01K 39/01 |
| 2022/0386584 A1 | 12/2022 | Rykbost | |

* cited by examiner

*Primary Examiner* — Kimberly S Berona
*Assistant Examiner* — Steven J Shur
(74) *Attorney, Agent, or Firm* — Grossman, Tucker, Perreault & Pfleger, PLLC

(57) ABSTRACT

An insect dispensing device and a method of using the same to feed a pet. More specifically, an insect dispensing device comprising an inlet, one or more outlets, passageways between said inlet and each said outlet, and a mechanism for occluding or opening a selected combination of said passageways.

20 Claims, 9 Drawing Sheets ical cut-away view of a preferred embodiment of the present invention where the insect dispensing device 10 may preferably have a plurality of first stacked pieces 20, a rotatable lid 30, a base 40, and a shell 50. As discussed in greater detail below, the insect dispensing device 10 may provide an inlet in the rotatable lid 30 through which the insects may be loaded. The insects may then travel through the inlet onto selected platforms 22 of the stacked pieces 20, and then out into the pet enclosure through opening 56 in the interior shell portion 51. In FIG. 1, the opening 56 in the interior shell portion 51 is seen on what may be described as the top level "A" of the device. It should be appreciated that there will be other similar openings on the interior of the shell for levels "B" and "C", which are not shown in the cross-sectional view provided in FIG. 1. As may also be appreciated, the interior shell portion 51 is configured to contain stacked pieces 20 and rotatable blocking piece 31, as herein described.

INSECT DISPENSING DEVICE

FIELD

The present invention relates to an insect dispensing device and a method of using the same to feed a pet. More specifically, the present invention relates to an insect dispensing device comprising an inlet, one or more outlets, passageways between said inlet and each said outlet, and a mechanism for occluding or opening a selected combination of said passageways.

BACKGROUND

Some pets, such as reptiles, are insectivores, meaning they will eat live insects. Pet owners with such pets often must dispense the live insects into their pets' enclosures. Pet owners may use a dispenser when dispensing the live insects into their pets' enclosure so as not to have to directly handle the insects. Pet owners may prefer to use a dispenser configured to contain the insects that can be placed within the enclosure and allow the insects to egress from the dispenser independently so as to further limit contact with the insects. Additionally, some pet owners coat the insects in a nutritional powder before dispensing them to provide the pet with additional nutrients besides those obtained by consuming the insect alone. Pet owners require ways of applying such a nutritional powder to live insects and dispensing them in the pet enclosure.

SUMMARY

An insect dispensing device comprising a plurality of first pieces each having a platform engaged to a hollow central shaft, the hollow central shaft portion having a perimeter and a height including an opening extending along a portion of the hollow central shaft perimeter and height. The device also includes a hollow blocking piece configured to fit within the hollow central shaft of the plurality of first pieces, wherein the hollow blocking piece has a height and a perimeter, including an opening extending along at least a portion of the hollow blocking piece height and perimeter.

A method of dispensing insects comprising supplying a plurality of first pieces each having a platform engaged to a hollow central shaft, the hollow central shaft portion having a perimeter and a height including an opening extending along a portion of the hollow central shaft perimeter and height. The device also includes a hollow blocking piece configured to fit within the hollow central shaft of the plurality of first pieces, wherein the hollow blocking piece has a height and a perimeter, including an opening extending along at least a portion of the hollow blocking piece height and perimeter. One may then position the opening on the hollow central shaft of the first pieces relative to the opening of the hollow blocking piece to selectively provide that the opening extending along a portion of the hollow central shaft is either open or closed.

DETAILED DESCRIPTION

With the foregoing in mind, the present invention relates to an insect dispensing device that may also be used as a decorative component of a reptile cage. More specifically, the present invention relates to an insect dispensing device comprising an inlet, one or more outlets, passageways between the inlet and each of the outlets, and a mechanism for selective occluding or opening some combination of the passageways. The passageways of the present disclosure may also preferably provide a space for the insects to be gathered where a nutritional powder may be applied to the insects. The nutritional powder may comprise vitamins, minerals or animal attractant.

Figure 1:
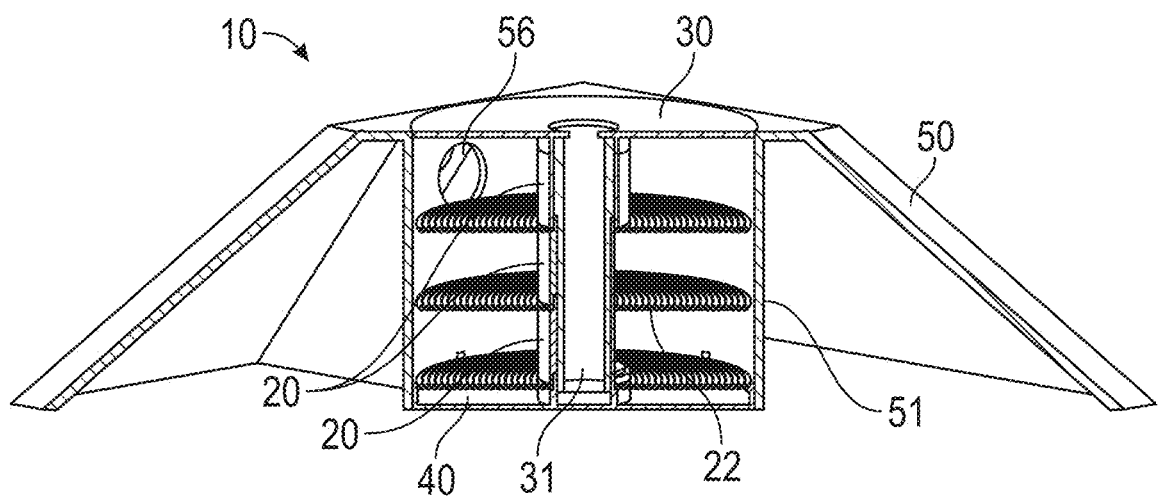
FIG. 1 depicts a cross-sectional cut-away view of a preferred insect dispensing device.

FIG. 1 depicts a cross-sectional cut-away view of a preferred embodiment of the present invention where the insect dispensing device 10 may preferably have a plurality of first stacked pieces 20, a rotatable lid 30, a base 40, and a shell 50. As discussed in greater detail below, the insect dispensing device 10 may provide an inlet in the rotatable lid 30 through which the insects may be loaded. The insects may then travel through the inlet onto selected platforms 22 of the stacked pieces 20, and then out into the pet enclosure through opening 56 in the interior shell portion 51. In FIG. 1, the opening 56 in the interior shell portion 51 is seen on what may be described as the top level "A" of the device. It should be appreciated that there will be other similar openings on the interior of the shell for levels "B" and "C", which are not shown in the cross-sectional view provided in FIG. 1. As may also be appreciated, the interior shell portion 51 is configured to contain stacked pieces 20 and rotatable blocking piece 31, as herein described.

As discussed further herein, the plurality of openings 56 on the shell 50 are selectively located on each level and the device allows the user to select which openings will in fact become active and available for the insects to emerge from the device. The stacked pieces 20 also preferably have openings on their platforms 22 to allow nutritional powder, which may be added into the device, to pass between the respective levels so that insects gathered on one or more of the levels may become coated in the powder when the device is shaken by the user.

The device 10 and its associated components (stacked pieces 20, platforms 22, lid 30, base 40 and shell 50) may preferably be made of polymeric material, such as thermoplastic and/or thermoset (crosslinked) polymer. For example, one may preferably form the device and the associated components from thermoplastic polymer such as polystyrene, acrylonitrile-butadiene-styrene (ABS), polyethylene, polypropylene, thermoplastic elastomers, etc.

Figure 2:
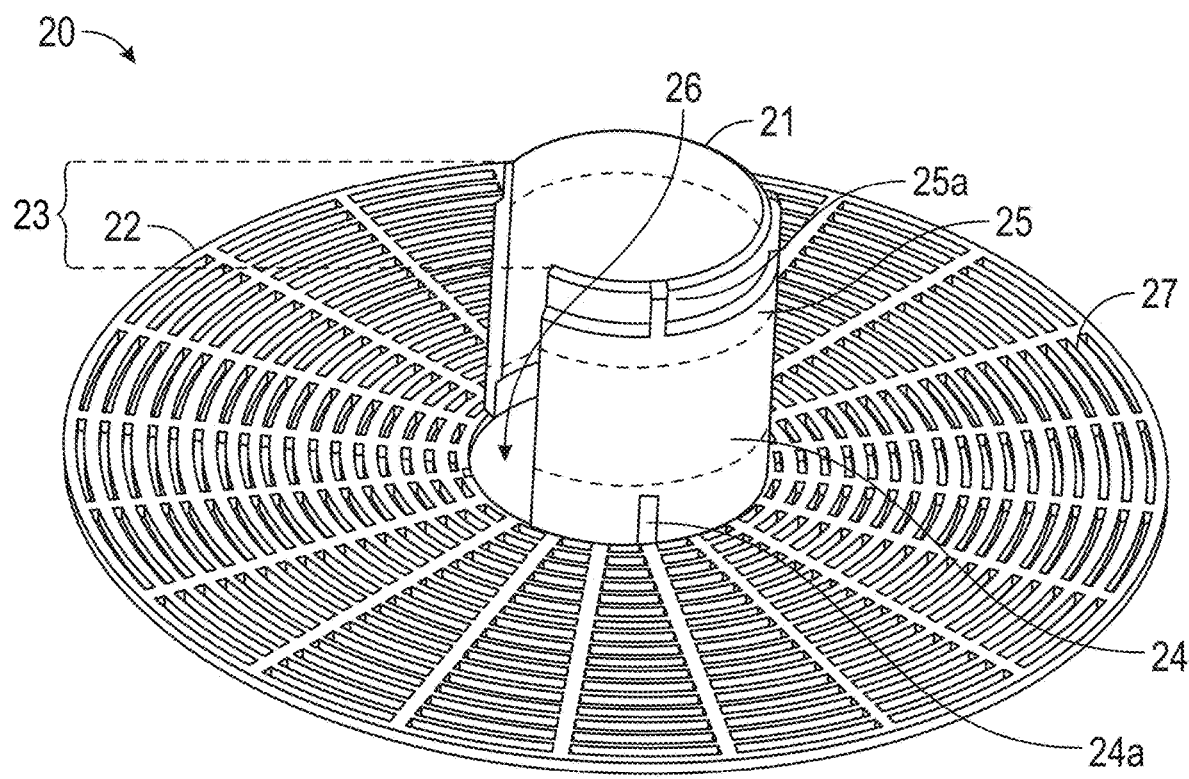
FIG. 2 depicts an exemplary first stacked piece of the embodiment of FIG. 1.

FIG. 2 depicts an exemplary first stacked piece 20 of the embodiment shown in FIG. 1. The stacked piece 20 preferably has a hollow central shaft 21 and a platform 22 engaged with the hollow central shaft. The platform preferably has a plurality of openings 27. The hollow central shaft also has an opening 23. The platform 22 preferably has a geometry of a square, rectangle, triangle, circle, oval, polygon, etc. More preferably, as depicted in FIG. 2, the geometry of the platform 22 may be circular. The platform 22 preferably has a thickness preferably in the range of 0.1" to 1.0", more preferably in the range of 0.2" to 0.4", and a width or diameter preferably in the range of 2" to 8", more preferably in the range of 3" to 4".

The platform 22 itself also preferably has an opening in a central region 26 so that it can be mechanically engaged to another similar stacked piece as disclosed herein. Such mechanical engagement with another similar stacked piece preferably occurs within the top region 25 and/or bottom region 24 of the hollow central shaft 21.

As alluded to above, the platform 22 preferably has a plurality of openings 27 that extend through the thickness of the platform 22 to allow a nutritional powder (e.g. a calcium enriched powder) placed within the insect dispensing device to pass between the openings 27 in the platform 22 and onto the insects gathered on adjacent slotted platforms. The plurality of openings 27 may be arranged randomly or in a pattern on platform 22. The openings 27 may have geometries, such as, but not limited to, squares, rectangles, triangles, circles, ovals, polygons, slots, etc. The plurality of opening may have substantially the same or different geometry and/or dimension. In the embodiment shown in FIG. 2, the plurality of openings 27 may be configured as arched rectangular shaped slots arranged in concentric circles around the opening in the central region 26 where the length of the openings 27 may increase radially from the opening in the central region 26 to the perimeter of the slotted platform 22.

As also shown in FIG. 2, the central shaft 21 is preferably a hollow tube. The central shaft 21 preferably has a cross-sectional geometry such as in the form of a square, rectangle, triangle, circle, oval, polygon, etc. More preferably, as shown in the embodiment of FIG. 2, the cross-sectional geometry may be a circle. The width or diameter of the cross-sectional geometry of the central shaft 21 is preferably in the range of 0.25" to 3.0", more preferably in the range of 1" to 2". The central shaft 21 may have a height preferably in the range of 0.25" to 3.0", more preferably in the range of 0.5" to 1" and a wall thickness preferably in the range of 0.1" to 0.5", more preferably in the range of 0.2" to 0.3".

The opening 23 in the wall of the hollow central shaft 21 extends along a portion of the hollow central shaft height and perimeter. More preferably, as shown in the embodiment of FIG. 2, the opening 23 may extend along the entire height of the hollow central shaft 21. The opening 23 in the hollow central shaft 21 preferably extends along 10% to 50% of the perimeter of the hollow central shaft 21, more preferably 20% to 30% of the perimeter of the hollow central shaft 21. In other words, the hollow central shaft 21 that is connected to the platform 22 is preferably a hollow structure, such as a tube, with a perimeter, where a portion of the tube is removed along the perimeter of the tube to provide opening 23.

The central hollow shaft 21 of each stacked piece 20 preferably has a bottom region 24 with a first mating recess feature 24a and a top region 25 with a second and protruding mating feature 25a. The first mating feature 24a and the second mating feature 25a of adjacent stacked pieces 20 are therefore preferably configured to mechanically engage one another.

Figure 3:
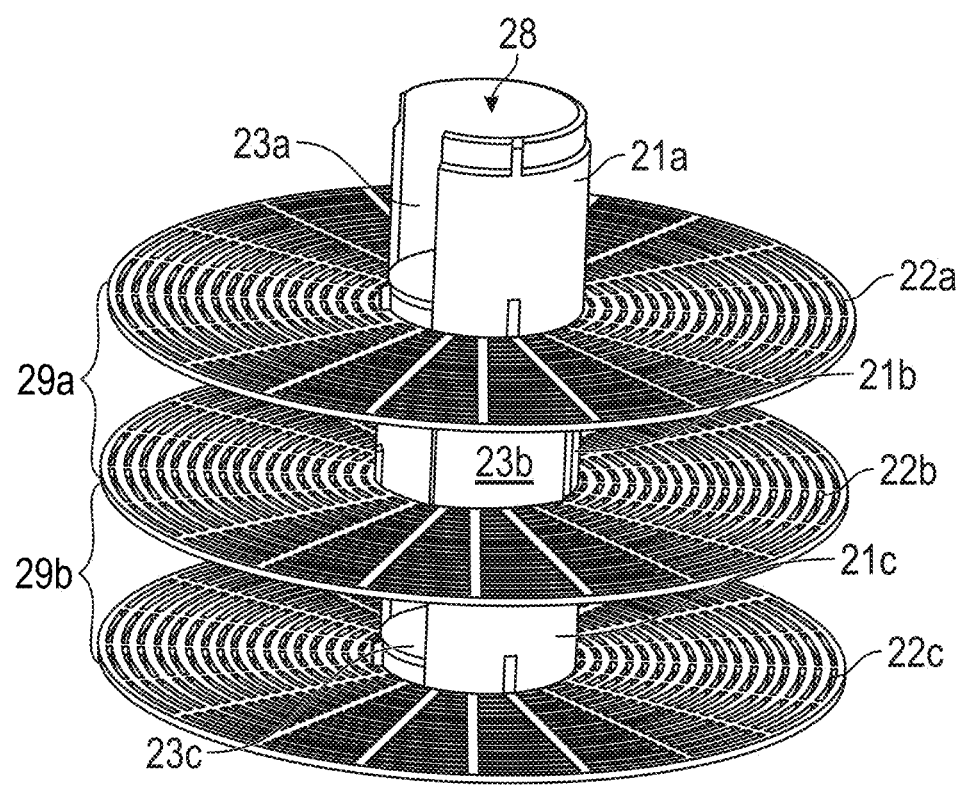
FIG. 3 depicts a plurality of stacked platforms of the embodiment of FIG. 1.

The plurality of stacked pieces 20 may be in the range of 2 to 10, more preferably in the range of 2-5. FIG. 3 depicts three (3) stacked platforms 22a, 22b, 22c of the embodiment of FIG. 1 mechanically engaged with one another. As can be appreciated from FIGS. 2-3, upon mechanical engagement of the first mating feature 24a and the second mating feature 25a of adjacent stacked platforms 22a, 22b, 22c, the hollow central shaft portions 21a, 21b, 21c of the adjacent stacked platforms 22a, 22b, 22c are preferably configured to create a combined hollow central shaft 28. When adjacent stacked platforms 22a, 22b, 22c are engaged, stacked areas 29a, 29b are preferably created between the platforms.

Moreover, the openings 23a, 23b and 23c in the hollow central shafts 21a, 21b and 21c of adjacent stacked platforms 22a, 22b, 22c may be selectively aligned or misaligned. That is, as shown in FIG. 3, the openings 23a and 23b are illustrated as preferably misaligned with respect to one another. Openings 23a and 23c are illustrated as preferably aligned with respect to one another.

Figure 4:
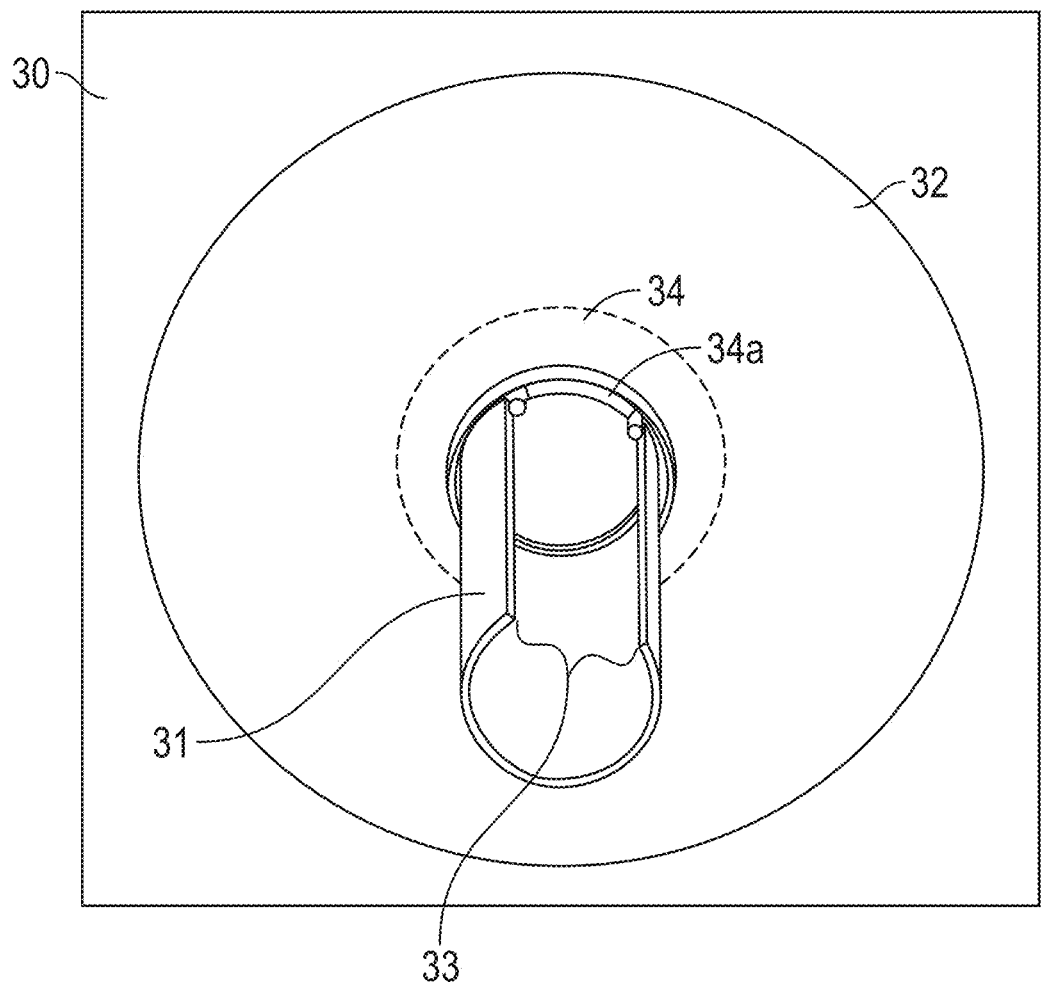
FIG. 4 depicts the solid plate and blocking piece.

FIG. 4 depicts the lid 30 of the embodiment shown in FIG. 1, preferably having a hollow blocking piece 31 engaged to a solid plate 32. The hollow blocking piece 31 is configured to fit within central shafts 21a, 21b and 21c of the adjacent stacked platforms 22a, 22b and 22c. The lid is rotatable along with the hollow blocking piece when positioned on the device 10 as shown in FIG. 1. The hollow blocking piece 31 of the lid 30 is preferably a hollow tube with an opening 33 where the opening extends along at least a portion of the hollow blocking piece height and hollow blocking piece perimeter. Preferably, the opening extends along the full length of the hollow blocking piece 31. The opening 33 in the hollow blocking piece 31 may therefore itself preferably define 10% to 50% the perimeter of the blocking piece wall or more preferably along 20-30% of the perimeter of the blocking piece wall. In other words, 10% to 50% of the perimeter of the hollow blocking piece is removed so that an opening 33 is indeed present in the hollow blocking piece 31. As also shown in FIG. 4, the solid plate 32 may have a central region with a mating feature 34a. Namely, mating feature 34a may fit within central shaft portion 21a (FIG. 3).

Figure 5:
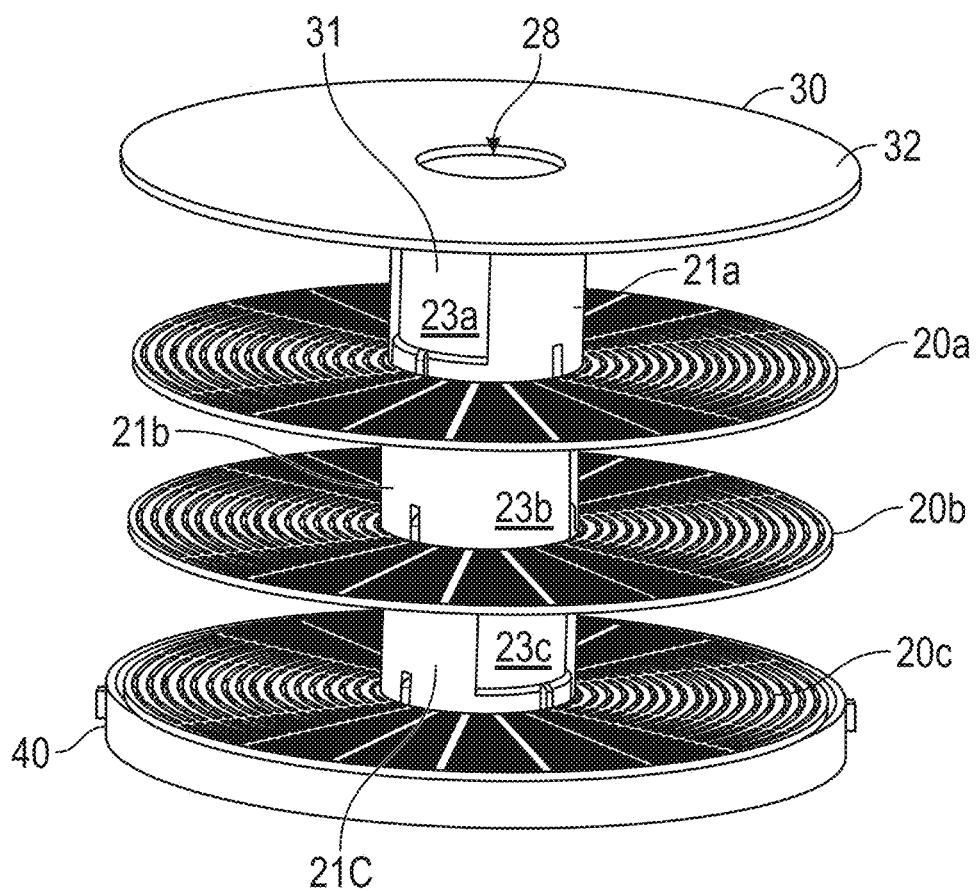
FIG. 5 depicts an assembled plurality of stacked pieces, rotatable lid and base of the insect dispensing device.

FIG. 5 next depicts the assembled stacked pieces 20a, 20b and 20c, rotatable lid 30, and base 40 of the embodiment shown in FIG. 1. As shown in FIG. 5, the hollow blocking piece 31 is preferably configured to fit within the central shaft 28 formed by the stacked pieces 20a, 20b, 20c so that it is substantially flush against the inner surface of the central shaft 28. The hollow blocking piece 31 of the rotatable lid 30 preferably has a length that is equal to the height of the central shaft 28 formed by the plurality of mechanically engaged stacked pieces 20a, 20b, 20c.

As may now be appreciated upon consideration of FIGS. 1-5, the solid plate 32 of the rotatable lid 30 with its blocking piece 31 is preferably configured to mechanically engage to stacked pieces 20a, 20b and 20c. Namely, the solid plate 32 with its blocking piece 31 is configured so that the hollow blocking piece 31 extends downwardly and into the device 10 (see again FIG. 1) and passes through hollow central shafts 21a, 21b and 21c. The blocking piece is therefore also rotatable. Accordingly, the openings 23a, 23b and 23c of the hollow central shafts 21a, 21b and 21c may be selectively positioned and aligned or misaligned with respect to one another, so that upon rotation of the rotatable lid and blocking piece 21, one or a plurality of the openings 23a, 23b or 23c can be selectively opened or closed to establish a pathway for the insects when loaded into the device to arrive on one or more of the selected platforms 22a, 22b, 22c (FIG. 4). In FIG. 5, by way of example, opening 23a is closed by the blocking piece 31, whereas the blocking piece leaves openings 23b and 23c intact. Accordingly, it can be appreciated that by positioning the plurality of pieces 20a, 20b and 20c where each has a platform engaged to the hollow central shafts 21a, 21b and 21c, relative to said hollow blocking piece 31, one can selectively provide that said openings extending along a portion of said hollow central shafts are either open or closed.

It should also be noted that the solid plate 32 of the rotatable lid 30 may preferably be a square, rectangle, triangle, circle, oval, polygon, etc. More preferably the solid plate 32 may have a substantially similar geometry as the slotted platform 22 of the stacked pieces 20. Even more preferably, the solid plate 32 may extend beyond the perimeter of the slotted platform 22 of the stacked piece 20 by a distance in the range of 0.05" to 1.0", more preferably in the range of 0.1" to 0.2". The solid plate 32 may have a thickness preferably in the range of 0.1" to 1.0", more preferably in the range of 0.2" to 0.4".

Figure 6:
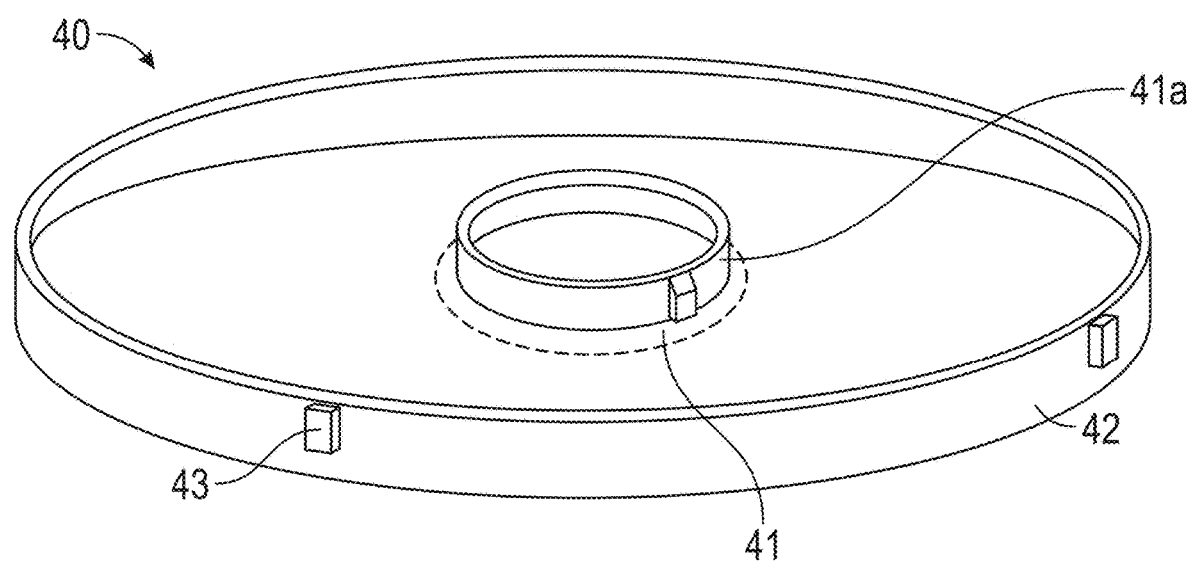
FIG. 6 depicts a perspective view of the base of the insect dispensing device.

FIG. 6 next depicts a perspective view of just the base 40. As shown in FIG. 6, the base 40 is preferably configured to mechanically engage a stacked piece 20c (FIG. 5). More preferably, the base 40 has a central region 41 having a mating feature 41a configured to mechanically engage a stacked piece 20c at a central shaft first mating feature 24a (see FIG. 2). The base 40 may preferably have a geometry of a square, rectangle, circle, oval, polygon, etc. More preferably, the base 40 may have a substantially similar geometry as the platform 22 of the stacked pieces 20. Even more preferably, the base 40 may extend beyond the perimeter of the platform 22 of the stacked piece 20 by a distance in the range of 0.05" to 1.0", more preferably in the range of 0.1" to 0.2". The base 40 may have a thickness preferably in the range of 0.1" to 1.0", more preferably in the range of 0.2" to 0.4". The base 40 preferably has a lip 42 extending substantially upright from the perimeter of the base 40. The height of the lip 42 may preferably be in the range of 0.1" to 2.0", more preferably in the range of 0.25" to 1.0". The lip 42 may preferably have a mating feature 43 configured to mechanically engage the shell 50 of the insect dispensing décor.

Figure 7:
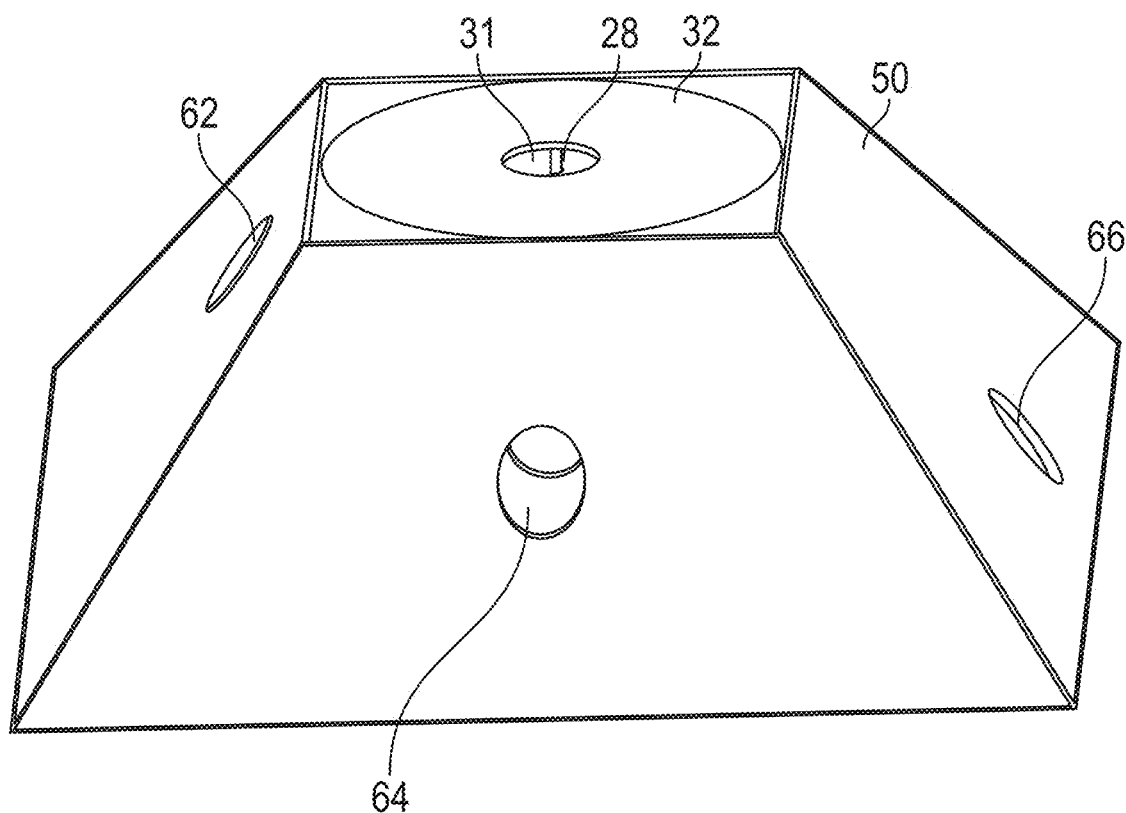
FIG. 7 depicts a view of the shell for the insect dispensing device.

FIG. 7 next provides another view of the shell 50 showing openings 62, 64, and 66 which openings selectively communicate with the openings 23a, 23b and 23c of the formed hollow central shaft 28. Accordingly, within the shell 50 are the assembled stacked pieces of FIG. 5. Also visible in FIG. 7 is a portion of the central shaft 28, the rotatable solid plate 28 and a portion of the blocking piece 31. Accordingly, a user may conveniently rotate the solid plate 28 and as noted above, select where insects may exit the shell 50, namely at one or more of the plurality of openings 62, 64 or 66. In other words, a shell 50 is provided having openings 62, 64, 66 wherein the openings are in communication with one or more of the openings 23a, 23b and 23c on said plurality of hollow central shaft portions 21a, 21b, and 21c (FIG. 3).

Figure 8:
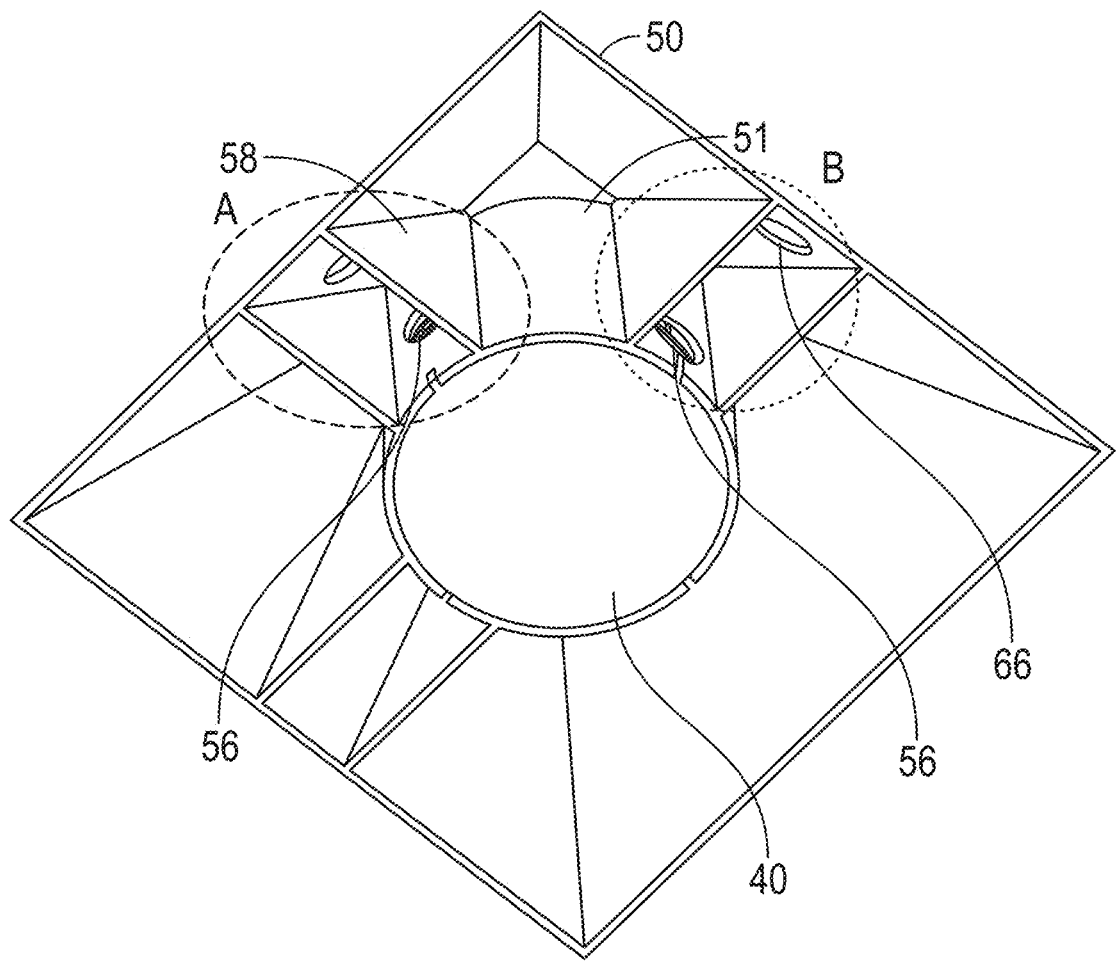
FIG. 8 provides a bottom view of the shell of the insect dispensing device.

FIG. 8 next provides a bottom view of the shell 50. As can be appreciated, the shell 50 preferably has a central core structure 51 (FIG. 1) that surrounds the plurality of platforms and includes openings 56 that are similarly in communication with one or more of the openings 23a, 23b and 23c on said plurality of hollow central shaft portions 21a, 21b and 21c (FIG. 3). The insects will therefore be able to exit through, e.g., one or more of the openings 56 on the central core 51 and then exit to the outside through one or more of the exits 62, 64 or 66 on the outside surface of the shell 50. Also, as seen in FIG. 8, there are preferably two rib structures 68 that extend from the core portion 51 to the outer shell portion 50 that isolate a selected pathway for the egress of the insects. Namely, the path circled and labelled "A" is isolated from the path circled and labelled "B."

Figure 9:
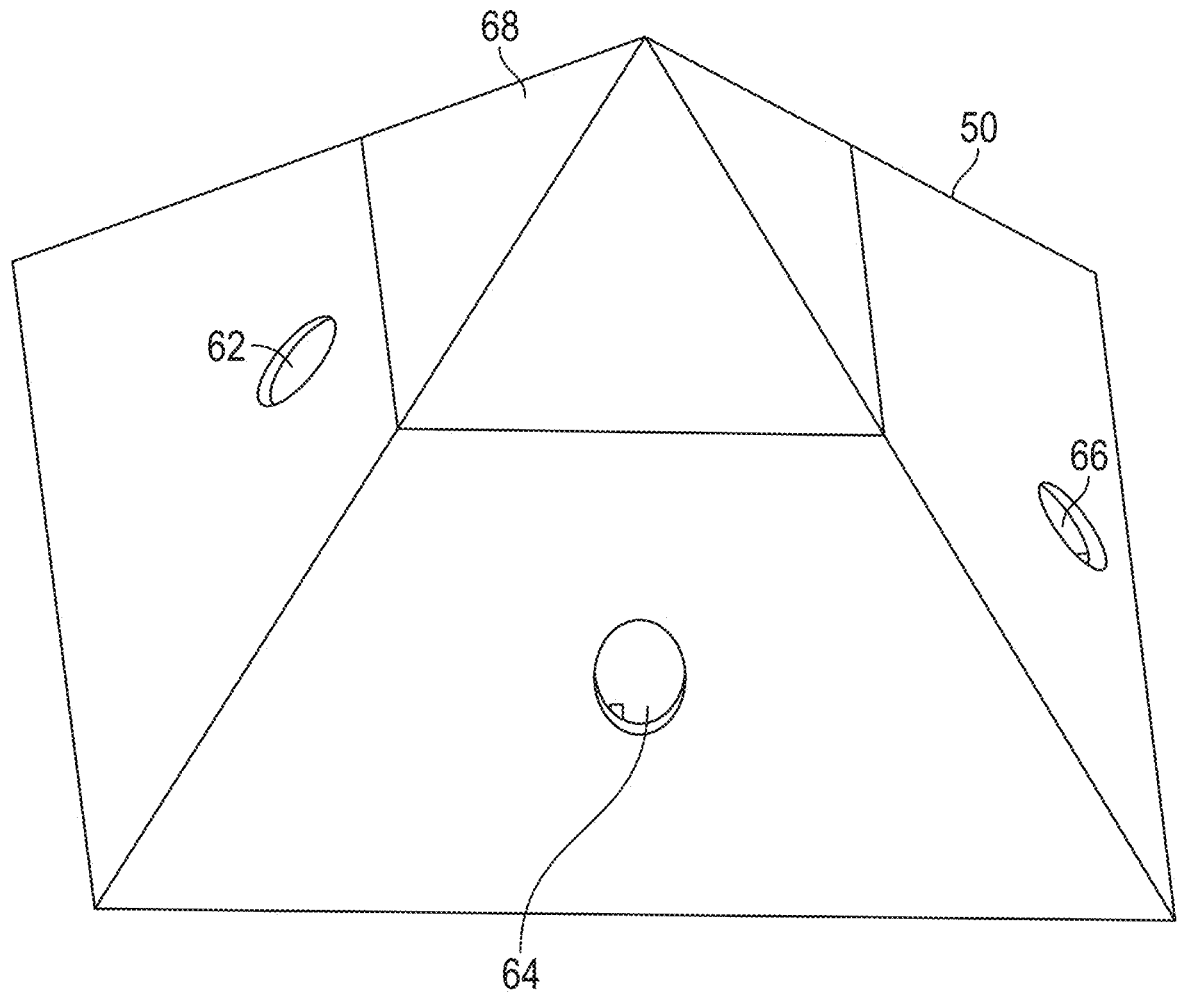
FIG. 9 provides a perspective view of the shell illustrated in FIG. 7 where a cap has been positioned on the top portion of the shell.

FIG. 9 provides a perspective view of the shell 50 illustrated in FIG. 7 where a cap 68 has been positioned on the top portion of the shell 50, so that it resembles a pyramid. As can therefore now be appreciated, the device 10 herein that selectively allows for the user to control the egress of insects on selected levels of the device, is one that can serve as a decorative component for a reptile enclosure. The device may therefore be configured into other types of décor within the reptile habitat while the egress of the insects through exits, such as exits 62, 64 and 66 shown in FIG. 9, are now less predictable.

What is claimed is:

1. An insect dispensing device comprising:
   a plurality of first pieces each having a platform engaged to a hollow central shaft, said hollow central shaft portion having a perimeter and a height including an opening extending along a portion of said hollow central shaft perimeter and height; and
   a hollow blocking piece configured to fit within said hollow central shaft of said plurality of first pieces, wherein said hollow blocking piece has a height and a perimeter, including an opening extending along at least a portion of said hollow blocking piece height and perimeter.

2. The insect dispensing device of claim 1 wherein said opening in said hollow central shaft of said plurality of first pieces extends along 10% to 50% of said perimeter of said hollow central shaft.

3. The insect dispensing device of claim 2 wherein said opening in said hollow central shaft of said plurality of first pieces extends along the entire height of said hollow central shaft.

4. The insect dispensing device of claim 1 wherein said opening in said hollow blocking piece extends along 10% to 50% of the perimeter of said hollow blocking piece.

5. The insect dispensing device of claim 4 wherein said opening in said hollow blocking piece extends along the entire height of said hollow blocking piece.

6. The insect dispensing device of claim 1 wherein said platform has a thickness and a plurality of openings extending through said thickness of said platform.

7. The insect dispensing device of claim 1 wherein said plurality of first pieces comprises 2 to 10 pieces.

8. The insect dispensing device of claim 1 wherein said openings in said hollow central shaft of said plurality of first pieces are aligned.

9. The insect dispensing device of claim 1 wherein said openings in said plurality of hollow central shaft of said plurality of first pieces are misaligned.

10. The insect dispensing device of claim 1 further including a shell having openings wherein said openings of said shell are in communication with one or more of said openings on said plurality of hollow central shaft portions.

11. The insect device of claim 10 further including a shell having an interior core portion that surrounds said plurality of platforms having one or more openings in communication with one or more of said openings on said plurality of hollow central shaft portions.

12. A method of dispensing insects comprising:
   supplying a plurality of first pieces each having a platform engaged to a hollow central shaft, said hollow central shaft portion having a perimeter and a height including an opening extending along a portion of said hollow central shaft perimeter and height including a hollow blocking piece configured to fit within said hollow central shaft of said plurality of first pieces, wherein said hollow blocking piece has a height and a perimeter, including an opening extending along at least a portion of said hollow blocking piece height and perimeter;

positioning said opening on said hollow central shaft of said first pieces relative to said opening of said hollow blocking piece to selectively provide that said opening extending along a portion of said hollow central shaft is either open or closed.

13. The method of claim 12 wherein said opening in said hollow central shaft extends along 10% to 50% of said perimeter of said hollow central shaft.

14. The method of claim 13 wherein said opening in said hollow central shaft extends along the entire height of said hollow central shaft.

15. The method of claim 12 wherein said opening in said hollow blocking piece extends along 10% to 50% of the perimeter of said hollow blocking piece.

16. The method of claim 15 wherein said opening in said hollow blocking piece extends along the entire height of said hollow blocking piece.

17. The method of claim 12 wherein said platform has a thickness and a plurality of openings extending through said thickness of said platform.

18. The method of claim 12 wherein said a plurality of pieces having a platform engaged to a hollow central shaft comprises 2 to 10 pieces.

19. The method of claim 12 further including a shell having openings wherein said openings are in communication with one or more of said openings on said plurality of hollow central shaft portions.

20. The insect device of claim 12 further including a shell having an interior core portion that surrounds said plurality of platforms having one or more openings in communication with one or more of said openings on said plurality of hollow central shaft portions.

* * * * *